United States Patent
Gerdes et al.

(10) Patent No.: US 10,850,276 B2
(45) Date of Patent: Dec. 1, 2020

(54) SYSTEMS AND METHODS FOR CAPTURE AND DETECTION OF LOW COPY TARGETS FROM LARGE SAMPLE VOLUMES

(71) Applicant: VisuGen Global LLC, Aurora, CO (US)

(72) Inventors: John C. Gerdes, Littleton, CO (US); Kirsten L. Nelson, Castle Pines, CO (US); Kris Buchanan, Fort Collins, CO (US)

(73) Assignee: VISUGEN GLOBAL LLC, Aurora, CO (US)

( * ) Notice: Subject to any disclaimer, the term of this patent is extended or adjusted under 35 U.S.C. 154(b) by 236 days.

(21) Appl. No.: 15/905,290

(22) Filed: Feb. 26, 2018

(65) Prior Publication Data

US 2018/0243738 A1    Aug. 30, 2018

Related U.S. Application Data

(63) Continuation of application No. PCT/US2018/019357, filed on Feb. 23, 2018.
(Continued)

(51) Int. Cl.
*B01L 3/00* (2006.01)
*B01D 15/22* (2006.01)
(Continued)

(52) U.S. Cl.
CPC ........ *B01L 3/502715* (2013.01); *B01D 15/22* (2013.01); *B01J 20/08* (2013.01);
(Continued)

(58) Field of Classification Search
CPC ......... B01L 3/502715; B01L 3/502761; B01L 3/00; B01D 15/22; B01J 20/08;
(Continued)

(56) References Cited

U.S. PATENT DOCUMENTS

| | | |
|---|---|---|
| 6,291,166 B1 | 9/2001 | Gerdes et al. |
| 6,838,005 B2 | 1/2005 | Tepper et al. |

(Continued)

OTHER PUBLICATIONS

International Search Report and Written Opinion for International (PCT) Patent Application No. PCT/US18/19357, dated Jul. 9, 2018 11 pages.
(Continued)

*Primary Examiner* — Brian J. Sines
(74) *Attorney, Agent, or Firm* — Sheridan Ross P.C.

(57) ABSTRACT

Systems and methods that enable the rapid identification of target molecules present in a sample at low concentrations is provided. The system includes a sample volume, and a detection structure that is connected to the sample volume by a conduit. The detection structure includes a microfluidic chip that defines a plurality of fluid channels. The walls of the fluid channels are formed from or covered with a metal oxide to which target molecules attach. After the sample volume has been passed through the detection structure, and in particular through the channels, visible microparticles are passed through the detection structure. The visible microparticles are configured to have an affinity for the target molecules. The microfluidic chip is then imaged to detect visible microparticles, and to thereby obtain information regarding the presence of the target molecules.

11 Claims, 11 Drawing Sheets

Related U.S. Application Data

(60) Provisional application No. 62/500,302, filed on May 2, 2017, provisional application No. 62/463,447, filed on Feb. 24, 2017.

(51) Int. Cl.

| | |
|---|---|
| *B01J 20/08* | (2006.01) |
| *G01N 15/06* | (2006.01) |
| *G01N 33/00* | (2006.01) |
| *G01N 33/48* | (2006.01) |
| *G01N 15/10* | (2006.01) |
| *B01J 20/28* | (2006.01) |
| *G01N 33/543* | (2006.01) |
| *G01N 35/00* | (2006.01) |

(52) U.S. Cl.
CPC ... *B01J 20/28028* (2013.01); *B01L 3/502761* (2013.01); *G01N 15/10* (2013.01); *G01N 33/54366* (2013.01); *G01N 35/00069* (2013.01); *G01N 35/00871* (2013.01); *B01J 2220/42* (2013.01); *B01L 2200/02* (2013.01); *B01L 2200/0647* (2013.01); *B01L 2300/069* (2013.01); *B01L 2300/0654* (2013.01); *B01L 2400/086* (2013.01); *G01N 2035/00158* (2013.01); *G01N 2035/00881* (2013.01)

(58) Field of Classification Search
CPC .............. B01J 20/28028; G01N 15/10; G01N 33/54366; G01N 35/0069; G01N 35/00871; G01N 21/00; G01N 15/06
See application file for complete search history.

(56) References Cited

U.S. PATENT DOCUMENTS

| | | | |
|---|---|---|---|
| 6,881,317 | B2 | 4/2005 | Huang et al. |
| 7,150,812 | B2 | 12/2006 | Huang et al. |
| 7,601,262 | B1 | 10/2009 | Tepper et al. |
| 8,425,254 | B2 | 4/2013 | Johannes |
| 9,500,625 | B2 | 11/2016 | Savran et al. |
| 2009/0053732 | A1 | 2/2009 | Vermesh et al. |
| 2012/0264646 | A1* | 10/2012 | Link .................... B01J 19/0046 506/11 |
| 2014/0045712 | A1* | 2/2014 | Link ...................... C12Q 1/686 506/9 |
| 2015/0056719 | A1 | 2/2015 | Karlovac et al. |
| 2015/0087079 | A1* | 3/2015 | Coffey ............. G01N 33/54366 436/501 |
| 2016/0054343 | A1 | 2/2016 | Holmes et al. |
| 2018/0105855 | A1* | 4/2018 | Paczkowski ...... B01L 3/502761 |

OTHER PUBLICATIONS

International Preliminary Report on Patentability for International (PCT) Application No. PCT/US2018/019357, dated Sep. 6, 2019, 8 pages.

\* cited by examiner

SECTION B-B

SYSTEMS AND METHODS FOR CAPTURE AND DETECTION OF LOW COPY TARGETS FROM LARGE SAMPLE VOLUMES

CROSS REFERENCE TO RELATED APPLICATIONS

This application is a continuation of PCT Application No. PCT/US18/19357, filed Feb. 23, 2018, and claims the benefit of U.S. Provisional Patent Application Ser. No. 62/463,447, filed Feb. 24, 2017, and U.S. Provisional Patent Application Ser. No. 62/500,302, filed May 2, 2017, the entire disclosures of which are hereby incorporated herein by reference.

FIELD

The present disclosure is directed to methods and systems for detecting target compounds present in water or other materials in small concentrations.

BACKGROUND

The detection and enumeration of microbial contaminants and pathogens, nucleic acids, protein antigens, or other biomolecules found in all manner of samples that include water, food, veterinary, clinical, military, and others is of tremendous importance to diagnosing and monitoring these specific targets since they can impact or threaten animal or human health. Frequently, the target molecule to be detected is found at copy numbers as few as one to 100 contained in from one milliliter to multiple liters of sample. This severely limits the sensitivity of target detection assays since testing protocols use microliter volumes that would not contain the target within the assay volume. Although sophisticated gene specific or immunoassay target detection methods are well known, there is a need for a means to concentrate and separate specific targets from milliliter to liter sample volumes. Furthermore, it would be of significant benefit if detection could be performed directly at the testing site using a simple, non-instrumented device with rapid results to enable more immediate actionable responses.

Affinity methods that combine solid phase capture reagents such as antibodies or aptimers specific to protein antigens or oligonucleotide probes specific to defined DNA or RNA sequences are well known as applied to column chromatography, ELISA or microarrays. Binding to immunomagnetic particles conjugated with specific binding reagents has also been described. However, none of these have been applied to processing greater than milliliter sample volumes especially for simple to use on site testing.

Capture of nucleic acids as well as viruses from samples can be accomplished using metal oxides such as aluminum oxide. Specifically, U.S. Pat. No. 6,291,166 to Gerdes et al. describes the use of certain metal oxides as a solid phase matrix material to capture and concentrate DNA or RNA using certain buffers. Alkaline conditions, high salt or chaotropes, and non-ionic detergents enhance DNA binding, while anionic (negatively charged) detergent or phosphate buffer blocked binding. There are also a number of published studies that confirm the nucleic acid binding properties of aluminum oxide. For example, Gerdes et al.'s technology can be adapted for a benchtop, single-tube nucleic acid extraction, amplification, and sequencing of hepatitis C virus. In addition, it is possible to use aluminum oxide membranes (AOM) mounted in wells as filtration "cards". Specifically, a lysate can be filtered through the membrane, washed, and then the membrane can be added to PCR tubes and target amplified by thermal cycling. Another technique involves using a DNA extraction chip with an AOM membrane. This technique can achieve an extraction efficiency of nearly 90% with raw blood samples.

Virus capture onto electropositive metal oxides directly from water is well known. For example, aluminum hydroxide large volume virus capture using membranes for water purification is discussed in U.S. Pat. Nos. 6,838,005 and 7,601,262. However, identifying particular viruses requires a cumbersome protocol for concentrating and eluting viruses from multi-liter volumes, which involves a complex lab procedure and does not integrate specific virus detection methods.

An approach for separating target cells from samples based on their size using specific microfluidic geometries of flow through devices have been discussed. For example, U.S. Pat. Nos. 6,881,317, 7,150,812, and 8,425,254 are generally directed to deterministic lateral displacement (DLD), which is a hydrodynamic technology that makes use of the asymmetric bifurcation of microfluidic laminar flow around obstacles to separate particles on the basis of size. In particular, DLD pillar arrays separate cells based upon differential flow rates based on particle size. By relying only on hydrodynamics, flow rates as high as 10 mL min-1 have been reported for the separation of cancer cells from blood.

An attractive approach for the detection and enumeration of targets directly on site could be the use of a cell phone. For example, a mobile imaging solution using a smartphone based fluorescent microscopy platform to analyze micro- and nano-scale objects is discussed in U.S. Patent Application Serial No. 2015/0056719. This field-portable platform utilizes a lightweight opto-mechanical hardware attachment that is installed on a smartphone. Using different snap-on hardware attachments, the platform can faithfully image *E. coli* in liquid samples, analyze blood samples to quantify red and white blood cells, and detect nano-scale particles such as viruses. However, such techniques do not allow specific molecules present in relatively small amounts in relatively large sample volumes to be detected with desired levels of accuracy and timeliness.

In summary, there is a need for a simple, inexpensive, integrated approach to concentrate and detect specific targets from large volume samples.

SUMMARY

The present disclosure is directed to systems and methods for the capture and detection of low copy target molecules from large sample volumes. Systems in accordance with embodiments of the present disclosure can include an adaptor structure, a reservoir of identification particles, a detection structure incorporating a microfluidic chip, a wicking member, and an imaging device. Methods in accordance with embodiments of the present disclosure can include collecting a sample volume of a liquid in a sample reservoir, connecting the sample reservoir to a detection volume incorporating a microfuidic chip, flowing the sample volume through the detection structure, flowing an identification fluid containing identification particles through the detection structure, and imaging the detection structure to determine the presence and concentration of target molecules by detecting identification particles that have been conjugated with target molecules.

More particularly, systems in accordance with embodiments of the present disclosure can include an adaptor structure that provides inputs to the detection structure. The adaptor structure can provide an inlet to which a container in the form of a sample reservoir can be connected to an inlet of a detection structure. In addition, the adaptor structure can include one or more reservoirs that contain an identification fluid, and can provide a channel from the one or more reservoirs to the inlet of the detection structure. The detection structure can include a microfludic chip. In accordance with at least some embodiments of the present disclosure, the microfluidic chip includes a plurality of pillars or other structures that define a plurality of fluid channels. The surfaces of the pillars are comprised of or are coated with a metallic oxide material having an affinity for a target molecule. An imaging device in accordance with embodiments of the present disclosure includes a light source and an image sensor. The imaging device can be configured to attach to or receive the detection structure. The light source can output light containing a wavelength or wavelengths that excite the imaging particles that have become bound to target molecules that have themselves become trapped to the microfluidic chip. The image sensor can be associated with a lens or other optical system such that a field of view of the image sensor encompasses the entire detection structure, allowing a concentration of target molecules in the sample volume to be determined from the presence and concentration of imaged identification particles.

Methods in accordance with embodiments of the present disclosure include detecting target molecules present in relatively low concentrations in relatively large sample volumes, without requiring time consuming amplification processes. Initially, a sample volume that may or may not contain a target molecule is collected. The container or sample reservoir in which the sample volume is collected can include a connector to which a length of tubing or other conduit can be connected. The sample reservoir is then connected to a detection structure incorporating a microfluidic chip having surfaces coated with a material to which the target molecule has an affinity. The sample volume is then passed through the detection structure. Next, a reservoir containing an identification fluid is connected to the detection structure, and the identification fluid is passed through the detection structure. The identification fluid includes identification particles that bind to the target molecule. A wicking member can be connected to an outlet of the detection structure, to facilitate drawing the identification fluid through the detection structure. The identification fluid can additionally include a dye or other substance that is visible when present in the wicking member, to facilitate determining whether the identification fluid has fully flowed through the detection structure. In accordance with at least some embodiments of the present disclosure, the sample reservoir and the reservoir containing the identification fluid can be connected to the detection structure via an adaptor structure that allows the identification fluid to be introduced to the detection structure without requiring that the sample reservoir be disconnected from the detection structure.

Additional features and advantages of embodiments of the present disclosure will become more readily apparent from the following description, particularly when taken together with the accompanying drawings.

DETAILED DESCRIPTION

Figure 1A:
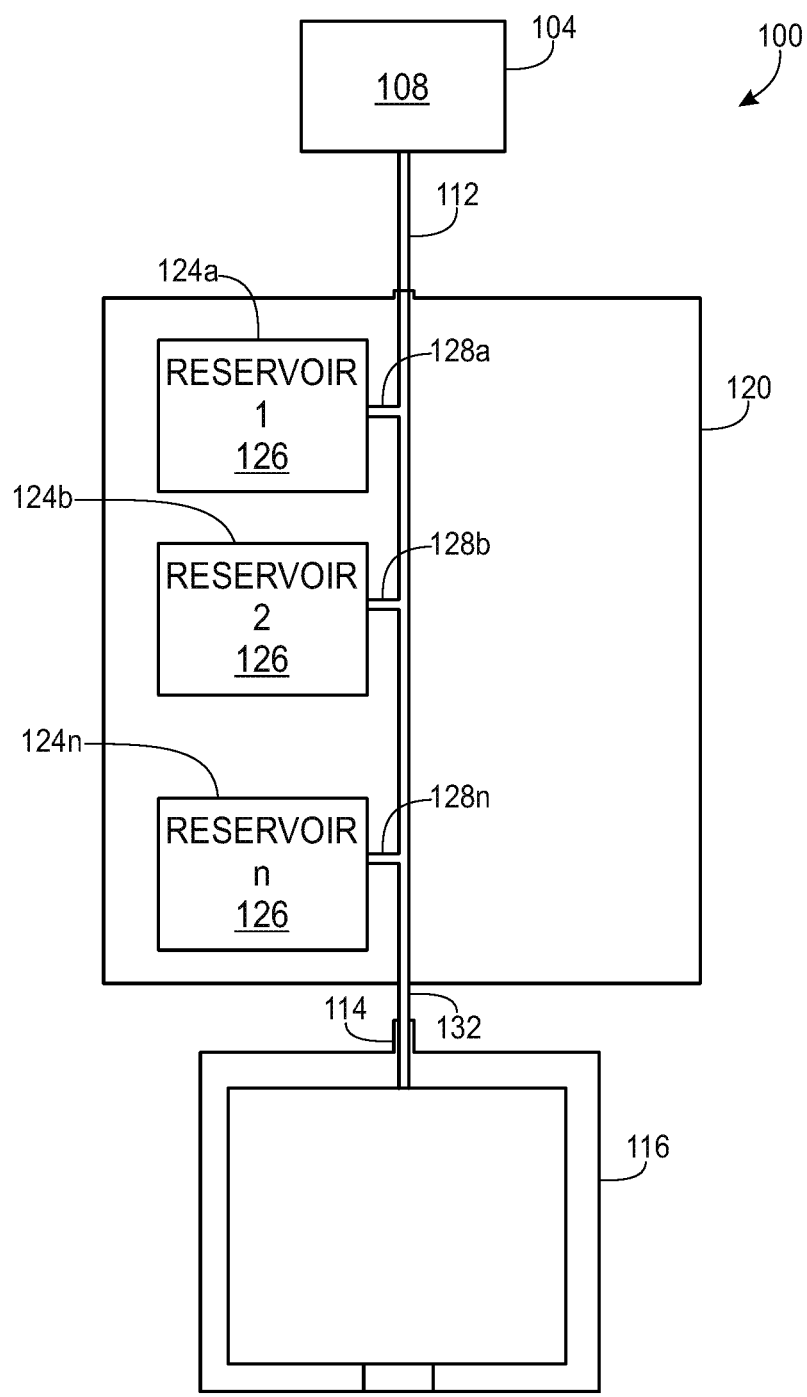
FIG. 1A is a block diagram depicting components of a system in accordance with embodiments of the present disclosure.
Figure 1B:
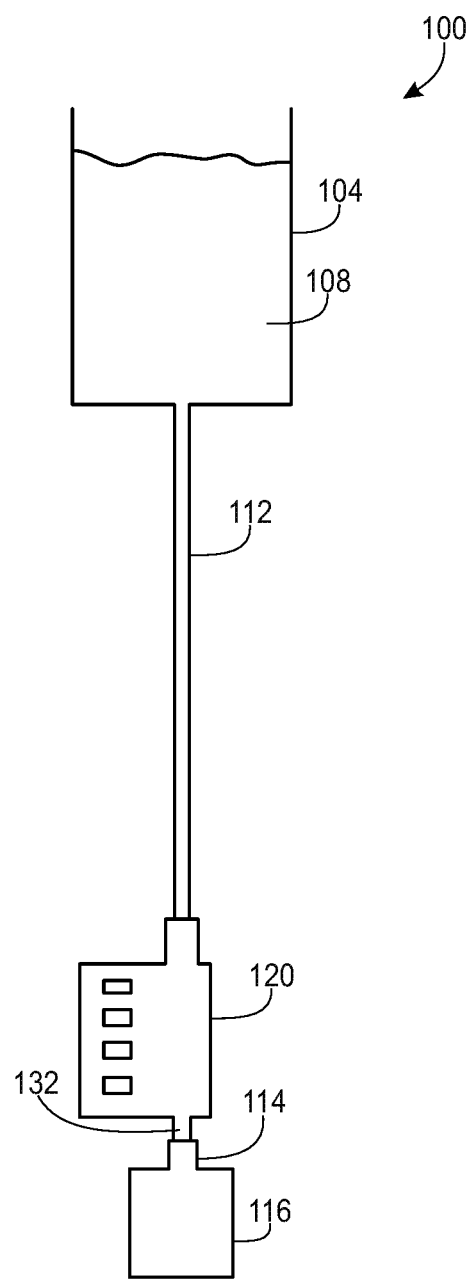
FIG. 1B depicts an exemplary embodiment of a system in accordance with embodiments of the present disclosure.
Figure 2:
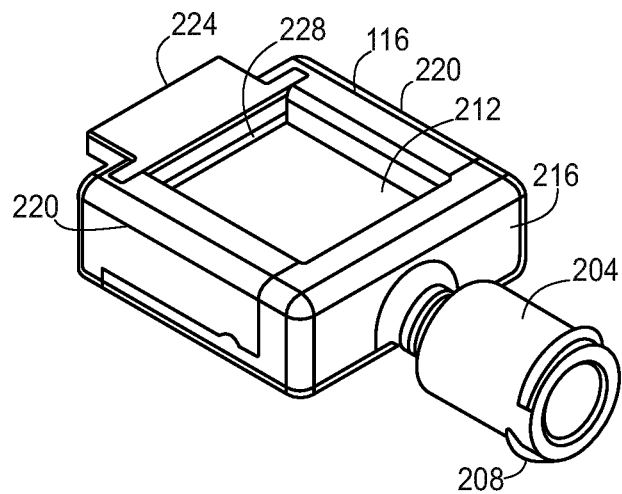
FIG. 2 depicts a detection structure in accordance with embodiments of the present disclosure in a perspective view.
Figure 3:
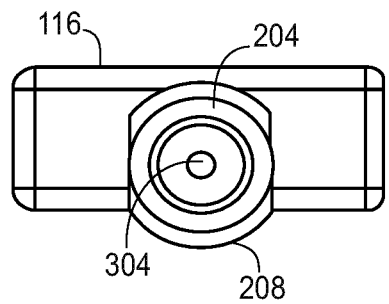
FIG. 3 depicts a detection structure in accordance with embodiments of the present disclosure in an end elevation view.
Figure 4:
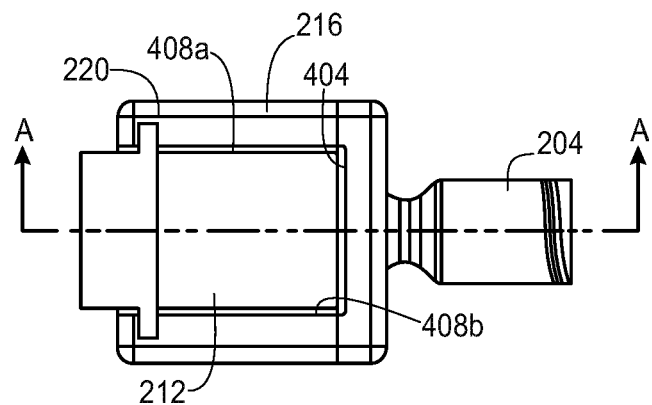
FIG. 4 depicts a detection structure in accordance with embodiments of the present disclosure in a top plan view.
Figure 5:
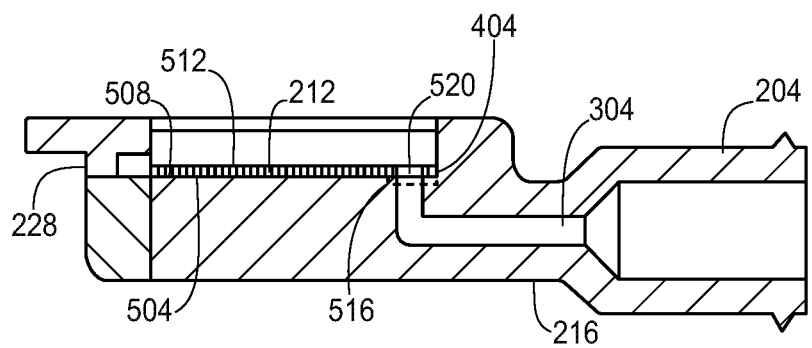
FIG. 5 depicts a detection structure in accordance with embodiments of the present disclosure take along section A-A line of FIG. 4.
Figure 6:
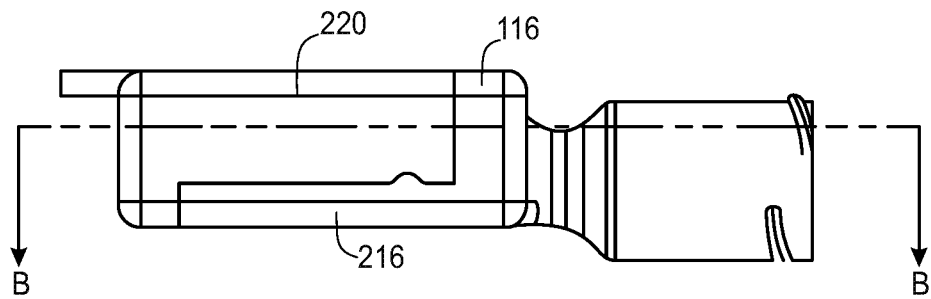
FIG. 6 depicts a detection structure in accordance with embodiments of the present disclosure in a side elevation view.
Figure 7:
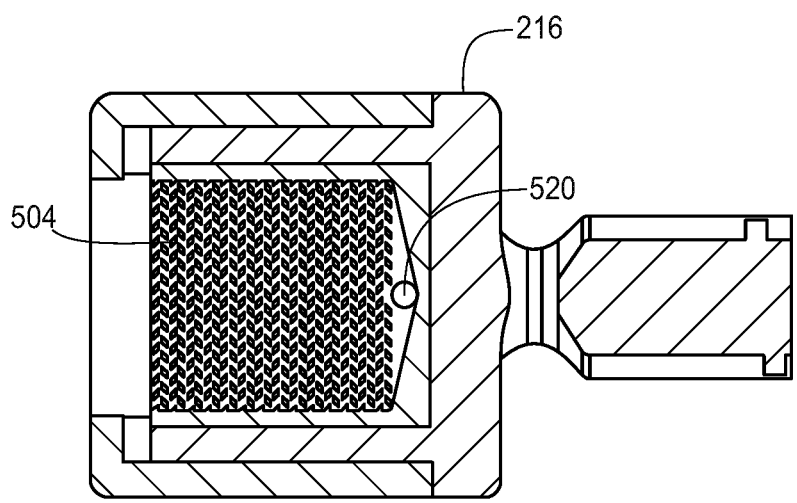
FIG. 7 depicts a detection structure in accordance with embodiments of the present disclosure take along section line B-B of FIG. 6.
Figure 8:
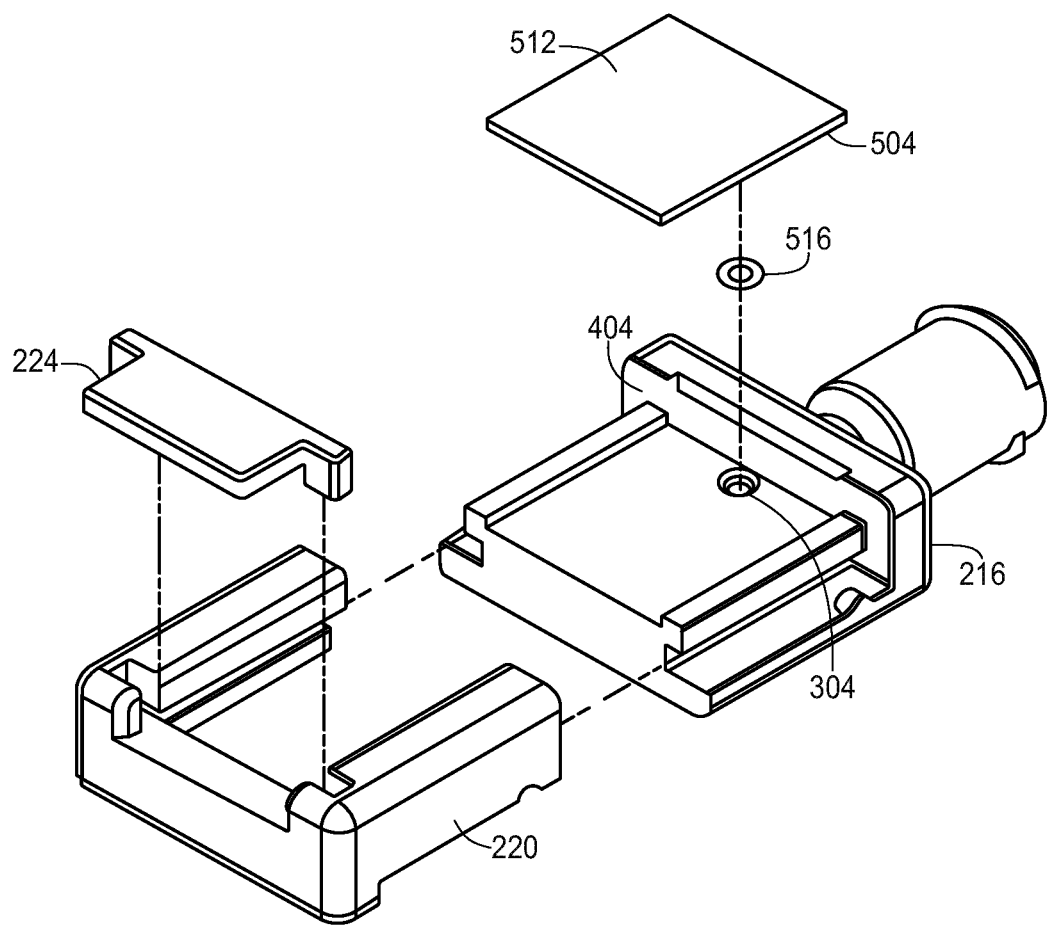
FIG. 8 depicts a detection structure in accordance with embodiments of the present disclosure in an exploded perspective view.
Figure 9:
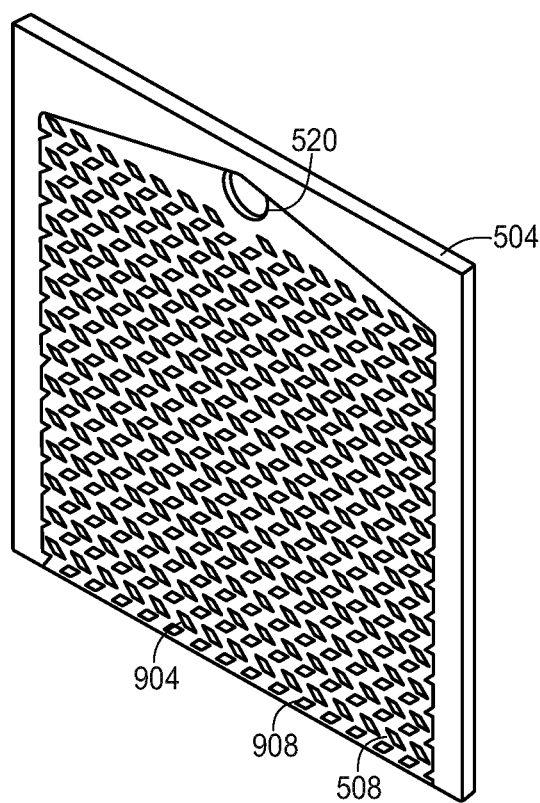
FIG. 9 depicts a microfluidic chip in accordance with embodiments of the present disclosure in a perspective view.
Figure 10:
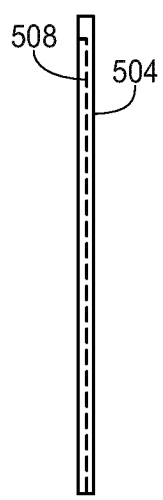
FIG. 10 depicts a microfluidic chip in accordance with embodiments of the present disclosure in a side elevation view.
Figure 11:
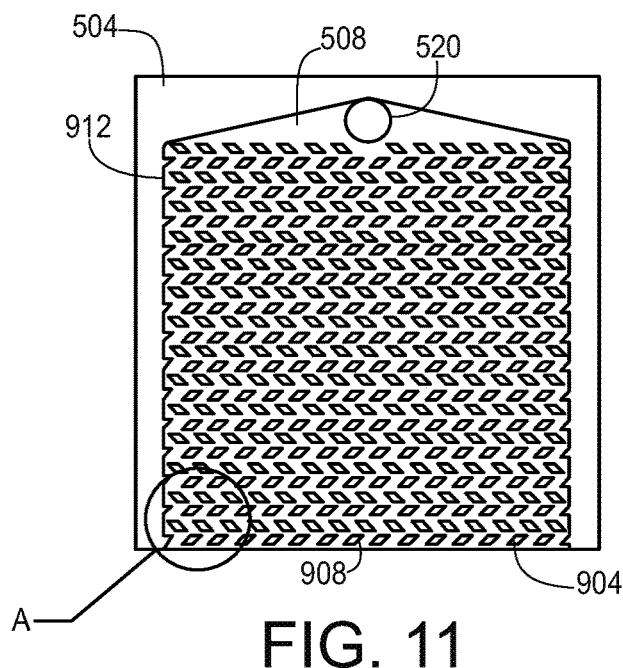
FIG. 11 depicts a microfluidic chip in accordance with embodiments of the present disclosure in a top plan view.

FIG. 1A is a block diagram depicting components of a system 100 for detecting copies of a target molecule, such as a biomolecule or virus. FIG. 1B depicts an exemplary embodiment of a system 100. The components generally include a container or sample reservoir 104 containing a sample volume 108, a conduit 112, an adaptor structure 120, and a detection structure or device 116. In accordance with at least some embodiments of the present disclosure, the conduit 112 can be connected to an inlet 114 of the detection structure 116 via the adaptor structure 120. As shown in FIG. 1A, and as discussed in greater detail elsewhere herein, the adaptor structure 120 can incorporate one or more identification fluid and/or was or buffer exchanges reservoirs 124 that that enable multiple assay steps and washes or contain an identification fluid 126. In addition, each identification fluid reservoir 124 can be associated with a Y-junction 128. Each Y-junction 128 includes a first input connected to the conduit 112, a second input connected to the associated identification fluid reservoir 124 containing identification particles, and an outlet that is connected to the inlet 114 of the detection structure 116 via an adaptor structure 120 outlet 132. In the example of FIG. 1A, three identification fluid reservoirs 124a, 124b, and 124n, and three corresponding Y-junctions 128a, 128b, and 128n, are shown. However, it should be appreciated that any number of identification fluid reservoirs 124 and Y-junctions 128 can be included in the system 100. In addition, the identification fluid 126 contained in each of the identification fluid reservoirs can be the same, for example to facilitate the detection of a target molecule in different samples 108, or the identification fluid 126 contained in each of the identification fluid reservoirs can be different, for example to allow for wash steps or buffer exchanges or for the detection of different target molecules in the same or different samples 108.

The sample volume 108 is typically a liquid that may or may not contain copies of a target molecule, such as a biomolecule or virus. As an example, and without limitation, the sample volume 108 may be a sample of water collected from an area suspected of being contaminated with E. coli bacteria. The sample reservoir 104 can be sized to hold a predetermined volume of liquid, and/or a known amount of the sample volume 108 can be placed in the container 104. The conduit 112 provides a fluid connection between the sample reservoir 104 and the detection structure 116. Moreover, as illustrated in FIGS. 1A and 1B, the connection may be completed via an adaptor structure 120. In accordance with at least some embodiments of the present disclosure, the conduit 112 is dimensioned, in length and/or diameter, to provide a predetermined amount of head pressure at the inlet 114 of the detection structure 116. In accordance with other embodiments of the present disclosure, the inlet 114 to the detection structure 116 can be connected in-line with a flow of water or other fluid comprising the sample volume. For example, the sample volume may be drawn from a stream or flow of the water or other fluid. In accordance with further embodiments of the present disclosure, a metered flow of a liquid comprising the target volume may be passed through the detection structure 116 via a pump.

The detection structure 116 is depicted in various views in FIGS. 2-8. In general, the detection structure 116 includes an inlet 204, with a connector 208, such as a Luer lock connector. A passageway 304 (see FIGS. 3 and 5) places the inlet 204 in communication with an identification volume 212. The identification volume 212 is at least in part defined by a microfluidic chip 504 base surface 508, and by a coverslip or top plate 512. The top plate 512 is transparent, at least to wavelengths associated with the identification particles contained in the identification fluid 126. In accordance with at least some embodiments of the present disclosure, a sealing member 516, such as an O-ring, is provided at an interface between the passageway 304 and an inlet aperture 520 formed in the base surface 508 of the microfluidic chip 504. A first end wall 404 of the identification volume 212 may be formed by a main frame member 216 of the detection structure 116. The sidewalls 408a and 408b of the identification volume 212 may be formed by lateral frame members 220. An end clip 224 is provided at an end of the identification volume 212 opposite the inlet 204. In accordance with the least some embodiments of the present disclosure, the end clip 224 can define an exit aperture 228 through which the sample volume 108 and other material can flow out of the identification volume 212.

Figure 12:
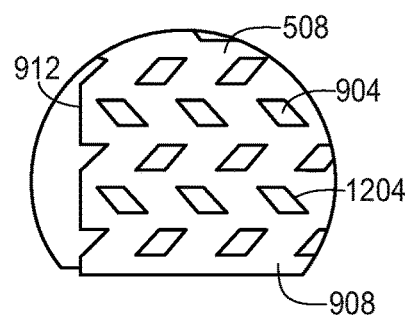
FIG. 12 is a detail of a channel structure of a microfluidic chip in accordance with embodiments of the present disclosure in a top plan view.

With reference now to FIGS. 9-12, additional features of the microfluidic chip 504 are depicted. In particular, the microfluidic chip 504 includes a plurality of pillars or walls 904 that extend from a base surface 508 that defines a portion of the identification volume 212. The pillars 904 have surfaces that define channels 908 therebetween. The pillars 904 are generally configured to promote contact between side surfaces 1204 of the pillars 904 and the molecules constituting the sample volume 108. At least the side surfaces 1204 of the pillars 904 are formed from, are coated with, or contain a metal oxide material that renders the microfluidic chip 504 selective for the capture of a selected target molecule or molecules. The base surface 508 and/or the surface of the coverslip 512 can also include the metal oxide material. Top surfaces of the pillars 904 may be bonded to the top plate 512, thereby forming the channels 908. For example, the top plate 512 can be bonded to the top surfaces of the pillars 904 by the application of heat and pressure. In accordance with at least some embodiments of the present disclosure, the pillars 904 are, in a plan view, configured as parallelograms. Moreover, the pillars 908 can be disposed in rows, with the parallelogram forms of the pillars 904 within a given row oriented in the same way. The pillars 904 in adjacent rows may comprise parallelograms oriented in a reverse orientation. The spacing between adjacent pillars 904 within a given row can be constant. Where the spacing causes a pillar 904 to intersect with a sidewall 912, the intersecting pillar 904 may be abbreviated or partially formed, for example as best shown in FIG. 12. Other configurations of pillars 904, which promote collisions between molecules in the sample volume 108 and the side surfaces 1204 of the pillars 904 are also possible. In accordance with at least some embodiments of the present disclosure, the pillars 904 are formed by depositing a metal oxide material on a substrate comprising the base surface 508 of the microfluidic chip 504. In accordance with alternate embodiments of the present disclosure, the microfluidic chip 504 is formed from injection molding, with pillars 904 that are integral to the base surface 508. In accordance with still other embodiments of the present disclosure, the microfluidic chip 504 is formed by a ceramic injection molding process.

Figure 13:
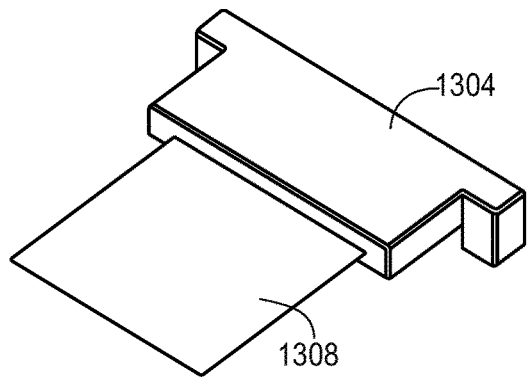
FIG. 13 depicts a wicking member in accordance with embodiments of the present disclosure.

The end clip 224 can be removed by a user, and replaced by a wicking member or structure 1304, depicted in FIG. 13. The wicking member 1304 is used in conjunction with the introduction of an identification fluid 126 from an identification fluid reservoir 124 to the detection structure 116. In particular, the wicking member 1304 includes a wicking material 1308 that creates a capillary flow that draws identification particles or microparticles included in the material 126 contained in the reservoir 124 through the channels 908 of the microfluidic chip 504. The identification particles are selected to bind to target molecules that have themselves been bound to the metal oxide material of the microfluidic chip 504. Those identification particles that do not bind with a target molecule attached to a channel 908 surface 1204 are drawn into the wicking material 1308. In addition, an indicator dye can be included in the wicking material 1308 as a control to ensure complete fluid flow through the microfluidic chip 504 by providing a visible indication to a user as to when the contents of the vial 124 have fully passed through the identification volume 212. Alternatively, unbound identification particles may be removed by adding a wash step prior to wicking. Other options for removing unbound particles include forcing air through the detection structure 116 using pressure or vacuum.

Figure 14:
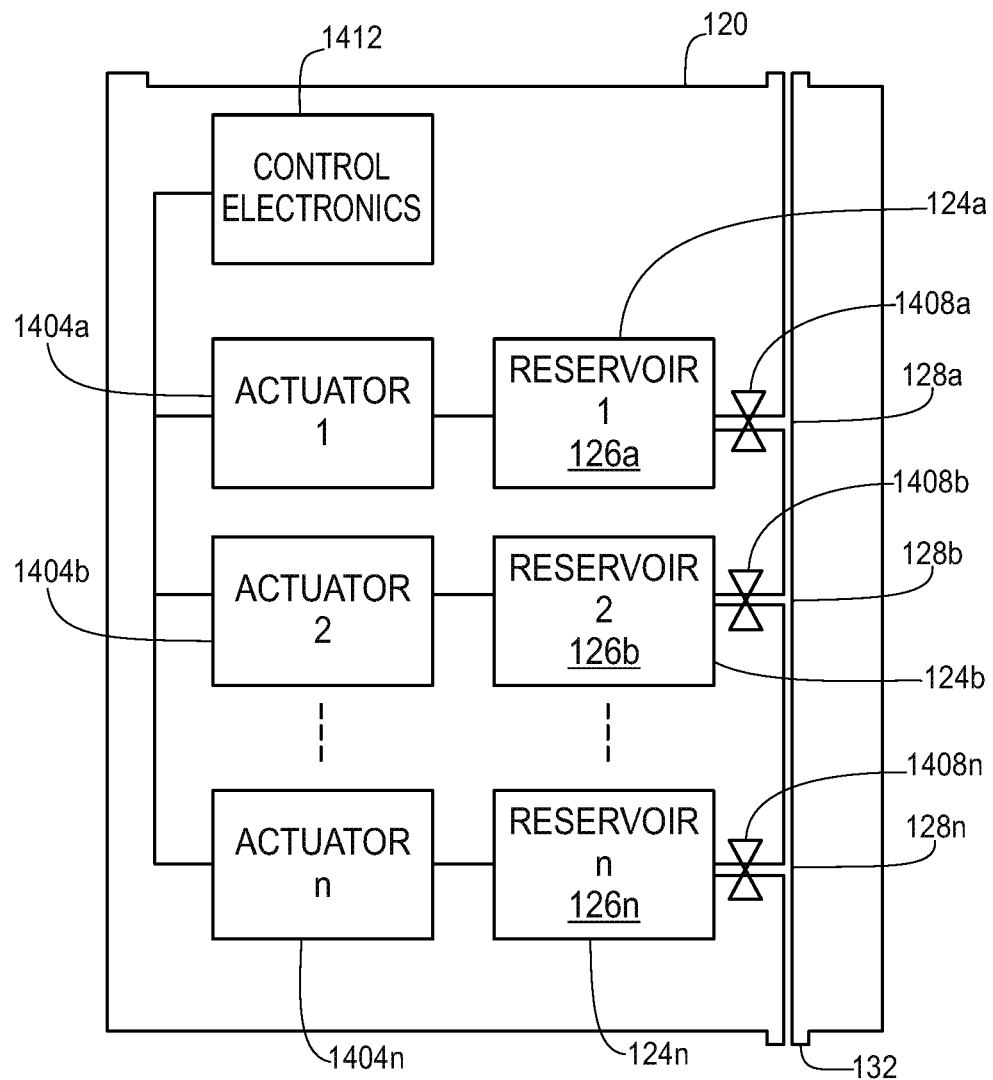
FIG. 14 depicts an adaptor structure in accordance with embodiments of the present disclosure.

With reference now to FIG. 14, an adaptor structure 120 in accordance with embodiments of the present disclosure is depicted. The adaptor structure 120 generally provides at least one Y-junction 128 to facilitate connecting an identification reservoir 124 containing an identification fluid 126 to an inlet 208 of a detection structure 116. Each Y junction 128 may comprise a set of microfluidic channels, with a first inlet in communication with the sample reservoir 104 via an inlet to the adaptor structure 120, a second inlet in selective communication with an identification fluid reservoir 124, and an outlet in communication with the detection structure 116 via an adaptor structure 120 outlet 132. The adaptor structure 120 can additionally include one or more identification fluid reservoirs 124, actuators 1404, and/or valves 1408, for selectively introducing an identification fluid 126 contained in an identification reservoir 124 to the detection structure 116. In at least some embodiments, the adaptor structure 120 provides identification fluid reservoirs 124 in the form of blister packs, where the reservoir 124 protrudes from a surface of the adaptor structure 120 such that it can be depressed by a user, increasing the pressure within the reservoir 124 to the point that a seal between the reservoir 124 volume and the second inlet of the Y-junction 128 is broken, allowing the identification fluid 126 to pass through the Y-junction 128 and into the detection structure 116. In accordance with further embodiments of the present disclosure, each fluid reservoir 124 can be associated with an actuator 1404. For example, a seal between a reservoir 124 in the form of a blister pack and the inlet 208 of the detection structure 116 can be acted on and ruptured using pressure applied by an actuator 1404 comprising a mechanical button. As another example, an actuator 1404 can be in the form of an electromechanical actuator that is activated in response to an electrical signal from control electronics 1412. Examples of control electronics 1412 include a general purpose programmable processor in combination with a memory. In addition, the control electronics 1412 can include an interface, such as a user input in the form of a hardware button or a button presented by a touch screen provided by the adaptor structure 120 or some other component, or by a smart phone, local computer, remote computer, network server, or other device connected to the adaptor structure 120 through a Bluetooth or other wireless interface, or a wire line interface. The electrical signal can be provided in direct response to the closing of a switch by a user, or through a signal sent by a controller 1408 in response to the closing of a switch by a user and/or the execution of instructions or control logic.

In accordance with embodiments of the present disclosure, different reservoirs 124 can contain the same or different identification fluids 126. For example, each reservoir 124 can contain the same identification fluid 126, for use with a series of sample volumes 108 and detection structures 116, for the detection of a common target molecule. In accordance with still further embodiments of the present disclosure, a single identification fluid reservoir 124 can be associated with an actuator 1404 and a valve 1408 that are operated by the control electronics 1412 to supply metered amounts of an identification fluid 126, allowing the adaptor structure 120 to be used with a series of different sample volumes 108 and detection structures 116. Alternatively or in addition, different identification fluid reservoirs 124 containing different identification fluids 126 can be provided as part of the adaptor structure 120, to allow for the detection of different target molecules within a sample volume 108 or a series of sample volumes 108 and detection structures 116. In accordance with still other embodiments of the present disclosure, reservoirs containing fluids other than identification fluids can be provided by an adaptor structure 120, can be connected to a detection structure via an adaptor structure 120, or can be connected to a detection structure 120 directly. For example, reservoirs containing fluids to prepare and/or remove molecules bound to the microfluidic chip 504 for further processing or identification, such as cDNA sequencing, can be provided.

Figure 15:
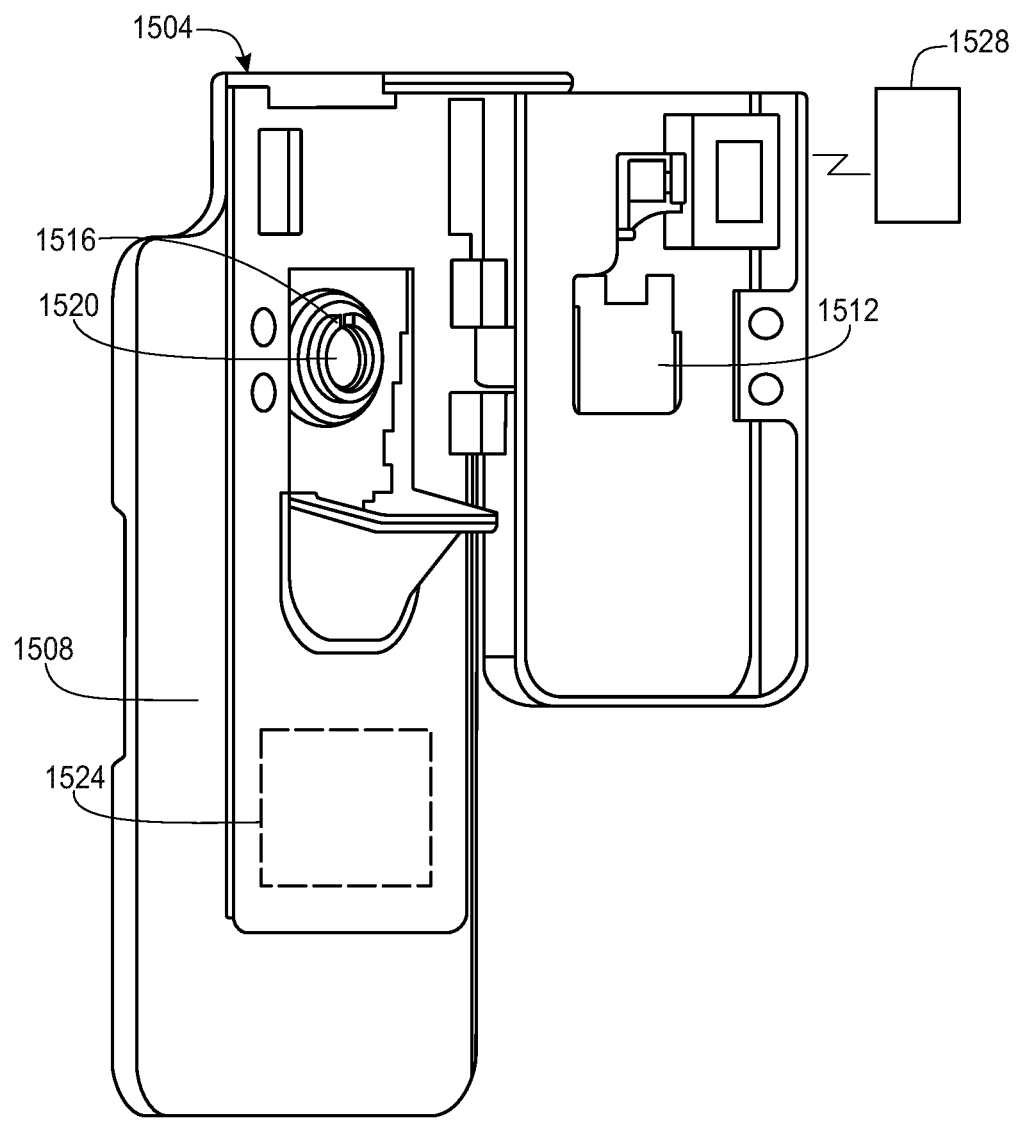
FIG. 15 depicts an imaging apparatus in accordance with embodiments of the present disclosure

An imaging apparatus 1504 in accordance with embodiments of the present disclosure is depicted in FIG. 15. The imaging apparatus 1504 generally includes an enclosure 1508 with a mount 1512 that is configured to receive the detection structure 116. In accordance with at least some embodiments of the present disclosure, the imaging apparatus 1504 includes a light source 1516, which can be activated to cause microparticles that have hybridized with target molecules attached to the channel 908 walls 1204 to fluoresce. The imaging apparatus 1504 can also include an image sensor 1520 configured to obtain an image of an installed detection structure 116 while the detection structure 116 is illuminated by the light source 1520. In accordance with embodiments of the present disclosure, the image sensor 1520 can include a focal plane array having a number of pixels and a lens system that images the entire area of the microfluidic chip 504 onto the focal plane array at one time. The imaging apparatus 1504 also generally includes control electronics 1524 that control operation of the light source 1516 and the image sensor 1520 to illuminate the microfluidic chip 504 and to take an image of the illuminated microfluidic chip 504. In particular, after the detection structure 116 has been placed in the enclosure 1408, the light source 1516 can be activated, and any resulting fluorescence detected by the image sensor 1520. The resulting image can be stored in memory included in the control electronics 1524. Alternatively or in addition, the control electronics 1524 can transmit the image to a connected device 1528, such as a smart phone that is connected to the imaging apparatus 1504 by a wireless connection, such as a Bluetooth connection, provided by a communications facility of the control electronics 1524. Alternatively, the image sensor 1520 may be provided as part of a larger device, such as a smart phone having a wide-angle camera, memory and a display. In accordance with embodiments of the present disclosure, the image can be analyzed using software or firmware running on the control electronics 1524, and/or can be provided to an app or program running on a connected device 1528, such as a smart phone, that can function to provide a count or other characterization of an amount of the target molecule in the sample volume 108.

Figure 16:
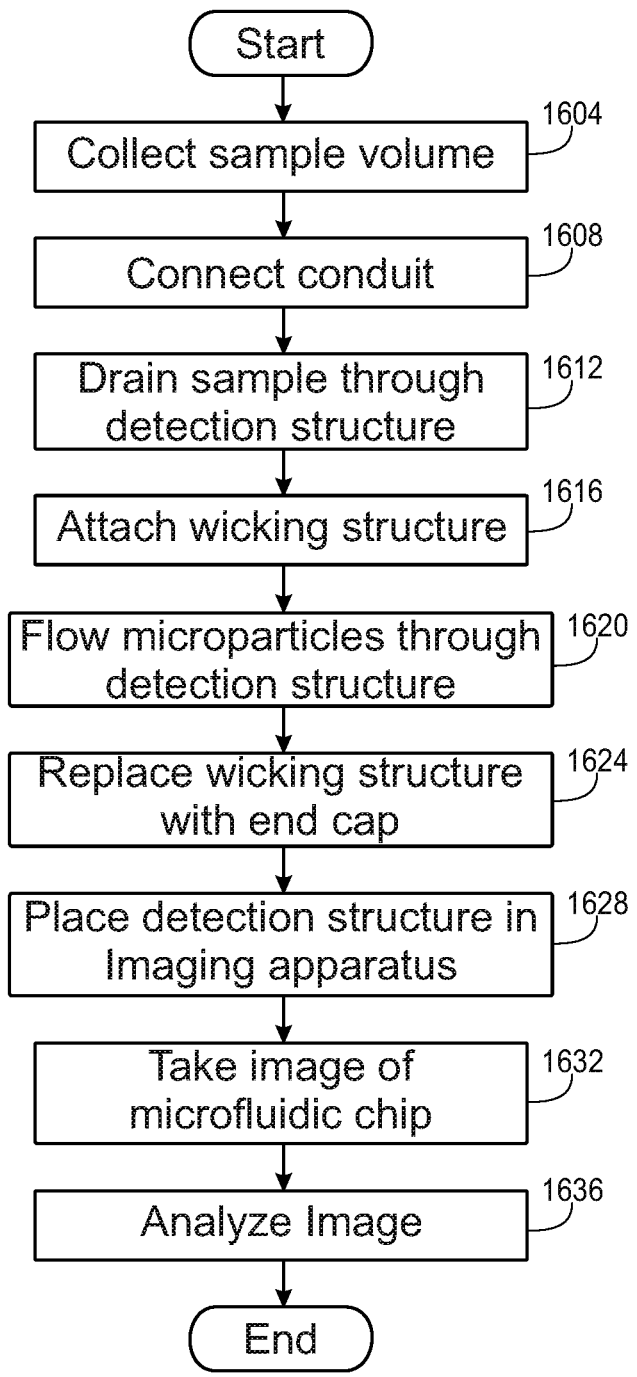
FIG. 16 is a flowchart depicting aspects of a method of detecting copies of a target molecule within a sample volume in accordance with embodiments of the present disclosure.

Aspects of the operation of a system 100 in accordance with embodiments of the present disclosure are depicted in FIG. 16. Initially, at step 1604, a volume of liquid to be analyzed as a sample volume 108 is collected and placed in a sample container 104. An outlet of the sample container 104 is connected to a conduit 112, which is in turn connected to the inlet 204 of a detection structure 116 via an adaptor structure 120 (step 1608). The sample container 104 is positioned over the detection structure 116, so that the conduit 112 is straight, and the sample volume 108 is allowed to drain from the container 104, down the conduit 112, through the adaptor structure 120, and through the detection structure 116 (step 1612). As can be appreciated by one of skill in the art after consideration of the present disclosure, by providing a conduit 112 having a predetermined length and inside diameter, the head pressure created at the detection structure 116 can be controlled, to provide a more consistent and reliable detection result. As described herein, the detection structure 116 includes a microfluidic chip 504 that presents a plurality of channels to the sample volume 108. Moreover, the channels are configured to promote contact between any target molecules included in the sample volume 108 and the side surfaces 1204 of the pillars 904 as the sample volume 108 flows across the microfluidic chip 504 and out the outlet 228 of the detection structure 116. All or a substantial portion (i.e. greater than 90%) of target molecules in the sample volume 108 that come into contact with a surface of the microfluidic chip 504 that comprise the metal oxide material to which the target molecule binds, such as the base surface 508 and the side surfaces 1204 of the pillars 904, are trapped to that surface.

At step 1616, an end 224 of the detection structure 116 is replaced by a wicking structure 1304. Next, a reservoir 124 of an identification fluid 126 containing identification particles or microparticles is placed in communication with the inlet of the detection structure 116 through a Y-connector 128 provided by the adaptor structure 120, and the identification fluid 126, including the identification particles, is allowed to flow through the detection structure 116 (step 1620). Placing the reservoir 124 in communication with the detection structure 116 can include opening a valve 1408 or fracturing a port, and can be the result of a manual process, or can be part of an electronically actuated process that is initiated in response to a manual input and/or an automated procedure implemented by or in association with control electronics 1412. In addition, at least some embodiments of the present disclosure allow an identification fluid 126 to be passed through a microfluidic chip 504 immediately after passing a sample volume 108 through the microfluidic chip 504, without requiring the manual connection or disconnection of a conduit or tubing. In accordance with embodiments of the present disclosure, the identification particles are coded to function as probes that attach themselves to specific molecules, including the target molecules. After the contents of the reservoir 124 have completely passed through the detection structure 116, as indicated by a dye visible in the wicking material 1308, the detection structure 116 is removed from the Y-connector 120, and the wicking structure 1304 is replaced by the end cap 224 (step 1624). Next, the detection structure 116 is placed in an imaging apparatus 1504 (step 1628). An image of the area of the detection structure 116 encompassing the microfluidic chip 504 is then taken (step 1632). Taking an image of the detection structure 116 can include illuminating the microfluidic chip 504 through the cover slip 512 with an identification signal comprising light from a light source 1516 that includes a wavelength selected to make any identification particles that have attached to target molecules bound to the surfaces of the microfluidic chip 504 within the identification volume 212 visible to the image sensor 1520, which has a field of view that encompasses the entire area of the microfluidic chip 504.

In addition, at least some embodiments of the present disclosure allow further detection and identification of target molecules, esp. target biomolecules such as nucleic acids, by sequencing of nucleic acid polymers bound to the microfluidic chip 504 after passing a sample volume 108 through the microfluidic chip 504. In an exemplary embodiment, a nucleic acid molecule bound to the microfluidic chip 504 may be initially copied by binding with a complementary primer nucleic acid molecule in the presence of a polymerase enzyme (e.g. a DNA or RNA polymerase, such as a Taq polymerase or reverse transcriptase). The nucleic acid copies created by the polymerase may be removed from the microfluidic chip 504 and further analyzed to detect and/or identify these nucleic acid molecules. This further analysis may include an amplification step (for example amplification by polymerase chain reaction amplification) before a detection or identification or quantification procedure is performed on the amplified nucleic acid products. Further analytical procedures known to those of skill in the art may be performed on the copied and/or amplified nucleic acid products, such as DNA sequencing (such as high-throughput or "next generation" DNA sequencing that typically relies on one or more fluorescent labels and a "one-channel chemistry" detection scheme (e.g. sold by Illumina), or hybridization assays using hybridized nucleic acids incorporating one or more detectable labels (such as fluorescent dyes (e.g., fluorescein, texas red, rhodamine, Alexa fluors, Spectrum dyes, and the like), quantum dots, radiolabels (e.g., 3H, 125I, 35S, 14C, or 32P), and colorimetric labels. Means of detecting such labels are well known to those of skill in the art. Thus, for example, radiolabels may be detected using photographic film or scintillation counters, fluorescent markers may be detected using a photodetector to detect emitted light and fluorescence microscopes. Colorimetric labels are detected by simply visualizing the colored label. Preferably, hybridizing nucleic acids comprise fluorescent labels and most preferably, in the context of a fluorescence in situ hybridization (FISH) assay.

Figure 17:
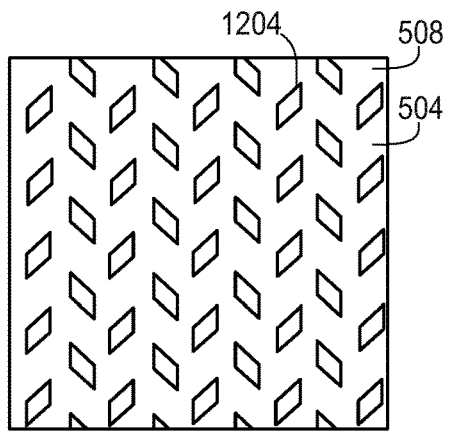
FIG. 17 is an image of a portion of a channel structure in accordance with embodiments of the present disclosure, in the absence of a target biomolecule.
Figure 18:
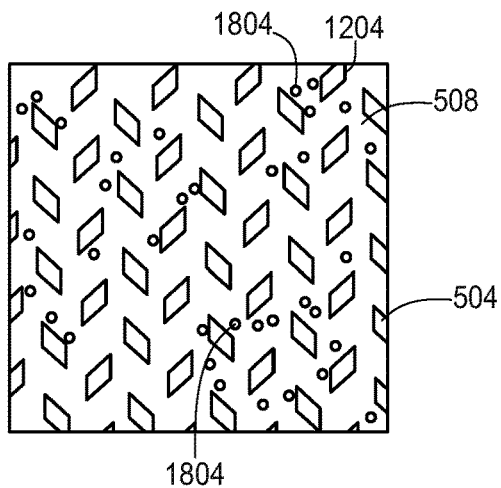
FIG. 18 is an image of a portion of a channel structure in accordance with embodiments of the present disclosure, after being exposed to a sample volume containing a target biomolecule.
Figure 19:
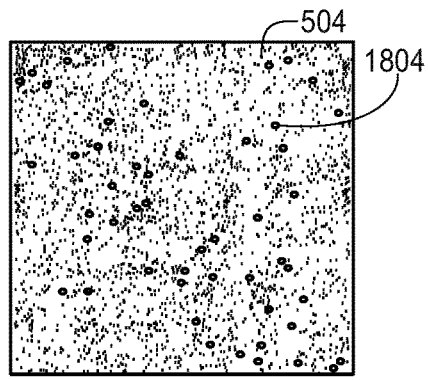
FIG. 19 is a fluorescent image of a portion of channel structure in accordance with embodiments of the present disclosure, after the channel structure has been exposed to a sample volume containing a target biomolecule.

As shown in FIG. 17, depicting a portion of a microfluidic chip 504, none of the identification particles will be present on the microfluidic chip 504 surfaces prior to passing the sample volume 108 through the detection structure 112, and none of the identification particles will be retained on the chip 504 after passing the sample volume 108 and identification fluid 126 through the detection structure 112 if no target molecules have attached themselves to the surfaces of the microfluidic chip 504. In contrast, as depicted in FIG. 18, if target molecules 1804 have attached themselves to surfaces 508 or 1204 within the detection structure 116, those target molecules 1804 will hybridize with at least some of the visible identification particles. Accordingly, the image sensor 1520 will be able to detect light associated with the identification particles that have bound themselves to the target molecules that are attached to the surfaces 508 and/or 1204 of the microfluidic chip 504. FIG. 19 depicts the area of the image shown in FIG. 18, at wavelengths encompassing only those of the identification particles that have been bound to target molecules 1804 attached to the chip 504.

At step 1636, a process running on the control electronics 1524 of the imaging apparatus 1504 or an app running on a connected smart phone or other device 1528 can function to analyze the image, and to provide a characterization of the number and/or concentration of target molecules 1804 in the sample volume 108 that have been made visible by being attached to identification particles. In accordance with still other embodiments, different microparticles, having different visible characteristics and affinities to different target molecules can be passed through the detection structure, permitting different molecules within a detection structure 116 to be identified. The process can then end.

Although different, separable components of a system 100 have been described and illustrated, it should be appreciated that other configurations are possible and are encompassed by the present disclosure. For example, an adaptor structure 120 can be integral to a detection apparatus 1504. In such embodiments, the detection structure 116 can be simultaneously connected to the adaptor structure 120 and positioned for imaging by the imaging device 1504. In addition, an enclosure 1508 can be configured to receive a smart phone 1528, and to use an image sensor provided by the smart phone 1528, for imaging operations. In accordance with still other embodiments, an adaptor structure 120 and/or a wicking member 1304 can remain attached to the detection structure 116 during illumination and imaging of the chip 504.

As described herein, in accordance with an exemplary embodiment of the present disclosure, the surfaces 1204 of the microfluidic chip 504 are formed from or coated with aluminum oxide, rendering the surfaces attractive to a range of molecules, such as biomolecules. For an exemplary embodiment of the present disclosure that is effective at detecting E. coli, the identification particles can comprise 10 micron fluorescent microparticles comprising 25 base pair E. coli specific capture probes attached to microparticles labeled with dragon green (Bangs) that exhibit specific binding with target biomolecules comprising E. coli DNA of complementary sequence captured by the aluminum oxide matrix of the microfluidic chip 504. The microfluidic chip 504 may have an area of 10 mm by 10 mm, and channels having a width of 200 microns. The conduit 112 can comprise 19 inches of tubing. The target sample 108 can comprise some number of E. coli cells, and can passed by gravity flow through the detection structure 116 at a flow rate of 20 milliliters per minute. Accordingly, passing a 100 milliliter target sample 108 through the detection structure 116 in this example requires five minutes. The enclosure 1508 and the imaging sensor 1524 may be configured such that the entire area of the microfluidic chip 504 is imaged simultaneously.

In accordance with still other embodiments, a sample may be analyzed for the presence of a target biomolecule. Moreover, embodiments of the present disclosure may be used to analyze a continuous flow of a fluid of indeterminate volume to determine whether a target biomolecule is present within the fluid.

The present disclosure provides systems and methods to accomplish superior target biomolecule detection sensitivity by means of combining the (a) use of large volumes to increase input sample target copy number, (b) selectively capturing and concentrating the target within channels by means of flow through binding within a component of specific geometry that promotes molecule deflective fluid flow and selective capture upon collision to channel walls, (c) specifically capturing a target recognition conjugated fluorescent or visable microparticle to the channel bound target, and (d) counting the captured microparticles by means of a wide field of view cell phone detector. Superior sensitivity is accomplished through the invention device strategy that combines large volume input, target capture and concentration, and wide field optical viewing of the entire area of the capture chip.

Certain embodiments of the present disclosure are discussed herein by way of example. In one embodiment E. coli is targeted as an indicator of fecal contamination whereby 100 milliliters of environmental, irrigation, or recreational water is added to a container 104 containing a lysis reagent that releases RNA and DNA from the targeted E. coli cells. The container 104 is drained through tubing 112 of sufficient length to create adequate pressure for gravity flow when connected to a luer lock cassette or detection structure 116 directly or via an adaptor structure 120. The detection structure 116 incorporates a flow through chip 504 of specific composition and geometry to enhance collision and capture of the RNA and DNA onto metal oxide channel walls during fluid flow. The sample bag or container 104 is detached from the detection structure 116 housing and a reservoir containing a colloidal suspension of fluorescent or visible micro-particles is placed in communication with the detection structure 116. A cap or wicking structure 1304 that contains a wicking material 1308 is attached to the other end of the cassette 116 to create capillary flow so that the identification particles flow through the channels of the chip 504. An indicator dye is used as a control to ensure fluid flow. As the micro-particles are conjugated with oligonucleotides specific to E. coli target sequences if they were captured from the water onto the channel walls they are captured by hybridization within the chip. The cassette or detection structure 116 is then inserted into an optical detector or imaging apparatus or device 1504 that can visualize the entire wide field view of the chip 504 and analyze the number of captured micro-particles that correlate with the input E. coli copy number of the water sample tested.

In one modification to the above embodiment sequences found in multiple copy number per E. coli cell as for example ribosomal RNA are targeted in order to further enhance detection sensitivity. In a further modification, specific to this approach the sample may be heated in order to selectively release small or ribosomal RNA from permeabilized cells with channel dimensions by design so that cell ghosts containing background DNA flow through the chip while the released RNA is captured onto the channel walls.

In at least some embodiments, the chip 504 is composed of metal oxide material manufactured for example by ceramic injection molding. A coverslip 512 compatible with fluorescent or other optical viewing is bonded onto the injection molded metal oxide for example aluminum oxide part and this flow through chip is housed within a detection structure 116 that includes a luer lock input and chip interface that provides for fluid flow. The aluminum oxide composition renders the chip selective for the capture on nucleic acid when the input water is adjusted to appropriate pH or buffer compositions as disclosed per Gerdes U.S. Pat. No. 6,291,166 or for the capture of viruses directly from water as disclosed in prior art publications (U.S. Pat. No. 6,838,005 B2, U.S. Pat. No. 7,601,262 B1), the contents of which are hereby incorporated herein by reference, at least as they pertain to the selective capture of molecules. The geometry of the aluminum oxide chip permits the concentration of nucleic acid present in low copy as it flows through the chip onto a localized area. By modifying the buffer (again per Gerdes U.S. Pat. No. 6,291,166) within the reservoir containing the visible particles with attached oligonucleotide probes, capture of the particles to target sequences or molecules on the channel walls occurs only if they hybridize to complementary sequences of the target organism. For the detection of a captured virus the detection microparticle can be conjugated with an antibody or aptimer or the captured virus nucleic acid can be released and bound to the aluminum oxide using a virus disruption buffer and then detected using oligonucleotide conjugated micro-particles.

In another embodiment, the water input volume and flow rates can be increased to sample liters of water by attaching the flow cassette 116 to a pump or by inserting it in line for continuous monitoring such as for monitoring water treatment plant effectiveness or assessing the safety of water reuse.

Those skilled in the field of molecular biology will readily recognize that embodiments of the present disclosure can be easily adapted by targeting other specific nucleic acid sequences for detection of additional microbes both of relevance to water testing such as the detection Enterococi to detect fecal contamination of salt water beaches or detection of specific pathogens such as *Salmonella, Shigella, E. coli* O157:H7. *Listeria monocytogenes*, and many others.

Those skilled in the field of molecular biology will also recognize that the embodiments of devices as disclosed herein can be applied to any biomolecule having specific binding recognitions such as antigen-antibody, or biomolecule-aptamer whereby one of the binding molecules is attached to flow through chip and device designs as disclosed herein but where the chip is of a polymer composition that can be coated by the binding molecule and manufactured with the specific geometry disclosed herein.

In accordance with at least some embodiments of the present disclosure, the technology encompasses:

(1) A method of detecting copies of a target molecule within a sample volume, comprising: providing a detection structure having multiple channels; passing the sample volume through the detection structure, wherein at least some of the copies of the target molecule within the sample volume become attached to at least some of the surfaces of the channels, and wherein the at least some surfaces of the channels have an affinity for the target molecule; passing a plurality of identification particles through the detection structure, wherein at least some of the identification particles become attached to the copies of the target molecule attached to the at least some of the surfaces of the channels; illuminating an area encompassing the multiple channels; and imaging the area encompassing the multiple channels, wherein a number of the identification particles that are attached to the copies of the target molecules attached to the at least some of the surfaces of the channels are detected by the imaging, and wherein the number of identification particles corresponds to a number of copies of the target molecule within the sample volume.

(2) The method of (1), wherein passing the sample volume through the detection structure includes: connecting an outlet of a container containing the sample volume to an inlet of the detection structure via a length of tubing; positioning the container above the detection structure; and allowing the sample volume to pass from the container through the detection structure.

(3) The method of any of (1) or (2) wherein the identification particles are selectively attached to specific target molecules.

(4) The method of any of (1) to (3), further comprising: after allowing the sample volume to pass from the container through the detection structure and before passing the plurality of identification particles through the detection structure, connecting a wicking member to an outlet of the detection structure.

(5) The method of (4), further comprising: after determining that a flow of the plurality of identification particles into the detection structure is sufficient, replacing the wicking member with a cap member, and wherein imaging an area encompassing the flow channels includes placing the detection structure in an imaging enclosure, illuminating the detection structure, and imaging the area of the detection structure encompassing the multiple channels.

(6) The method of any of (1) to (5), further comprising: removing unbound identification particles from the detection structure.

(7) The method of any of (1) to (6), wherein the multiple channels of the detection structure are provided at least in part by a microfluidic chip having a plurality of channels.

(8) The method of any of (1) to (7), wherein an inlet to the detection structure receives the sample volume from a stream of fluid.

(9) The method of (8), wherein the stream of fluid is provided via a pump.

(10) The method of any of (1) to (9), wherein the target molecules comprise nucleic acid molecules, further comprising:
directing the target nucleic acid molecule to a nucleic acid analysis methodology that detects or identifies or quantifies the target nucleic acid molecule.

(11) The method of any of (1) to (10), wherein the directing step comprises:
contacting the target nucleic acid molecules attached to the surfaces of the channels with a primer nucleic acid molecule and a polymerase enzyme to produce a target nucleic acid molecule copy; and,
directing the target nucleic acid molecule copy to a nucleic acid analysis methodology that detects or identifies or quantifies the target nucleic acid molecule copy.

In accordance with further aspects of the present disclosure, the technology encompasses:

(12) A detection device, comprising:
an inlet;
an identification volume;
a microfluidic chip, including a plurality of pillars extending from a base surface, wherein the pillars have a metallic oxide surface;
a top plate, wherein the top plate is bonded to the pillars of the microfluidic chip opposite the base channels to form a plurality of channels, and wherein the top plate, side surfaces of the pillars, and the base surface define at least a portion of the identification volume; and
an outlet.

(13) The detection device of (12), wherein the inlet is in communication with the identification volume via an inlet aperture formed in the base surface of the microfluidic chip.

(14) The detection device of (12) or (13), wherein the top plate is transparent.

(15) The detection device of any of (12) to (14), wherein at least most of the pillars have a parallelogram form.

In accordance with still further aspects of the present disclosure, the technology encompasses

(16) A system for detecting copies of a target molecule, comprising:
a sample reservoir;
a detection structure, including:
an identification volume, wherein at least one boundary surface of the identification volume is transparent to an identification signal;
an inlet to the identification volume;
a plurality of channels located within the identification volume, wherein at least some of the channels include a surface having an affinity for the target molecule; and
an identification volume outlet.

(17) The system of (16), further comprising:
an adaptor structure, including:
a first inlet;
an identification fluid reservoir;
an adaptor structure outlet, wherein the adaptor structure outlet is in communication with the inlet to the identification volume, wherein the first inlet places the sample reservoir in communication with the inlet to the identification volume through the outlet of the adaptor structure, and wherein the identification fluid reservoir is in communication with the inlet to the identification volume through the adaptor structure outlet.

(18) The system of (17) wherein the identification fluid reservoir contains an identification fluid, wherein the identification fluid includes a plurality of identification particles.

(19) The system of (17) or (18), wherein the adaptor structure includes a plurality of identification fluid reservoirs.

(20) The system of any of (17) to (19), further comprising:
an imaging device, wherein the imaging device includes:
a light source;
an image sensor, wherein the image sensor is sensitive to an identification signal.

(21) The system of (20), wherein the light source emits light of at least a first wavelength, wherein the identification signal is light of at least a second wavelength that is emitted by an identification particle in response to being illuminated with the light of the at least a first wavelength.

(22) The system of (20) or (21), wherein the imaging device includes a structure that receives the detection structure, and wherein the image sensor has a field of view that encompasses all of the plurality of channels of the detection structure.

The foregoing discussion has been presented for purposes of illustration and description. Further, the description is not intended to limit the disclosed systems and methods to the forms disclosed herein. Consequently, variations and modifications commensurate with the above teachings, within the skill or knowledge of the relevant art, are within the scope of the present disclosure. The embodiments described hereinabove are further intended to explain the best mode presently known of practicing the disclosed systems and methods, and to enable others skilled in the art to utilize the disclosed systems and methods in such or in other embodiments and with various modifications required by the particular application or use. It is intended that the appended claims be construed to include alternative embodiments to the extent permitted by the prior art.

What is claimed is:

1. A method of detecting copies of a target molecule within a sample volume, comprising:
providing a detection structure, including:
a microfluidic chip having a base surface, an inlet aperture formed in the base surface, and a plurality of pillars extending from the base surface, wherein surfaces of the pillars define a plurality of channels, and wherein at least some of the dim are surrounded by channels included in the plurality of channels;
passing the sample volume through the detection structure, wherein at least some of the copies of the target molecule within the sample volume become attached to at least some of the surfaces of the pillars, and wherein the at least some surfaces of the pillars have an affinity for the target molecule;
passing a plurality of identification particles through the detection structure, wherein at least some of the identification particles become attached to the copies of the target molecule attached to the at least some of the surfaces of the pillars;
illuminating an area encompassing the plurality of channels; and
imaging the area encompassing the plurality of channels, wherein a number of the identification particles that are attached to the copies of the target molecules attached to the at least some of the surfaces of the pillars are detected by the imaging, and wherein the number of identification particles corresponds to a number of copies of the target molecule within the sample volume.

2. The method of claim 1, wherein passing the sample volume through the detection structure includes:
connecting an outlet of a container containing the sample volume to an inlet of the detection structure via a length of tubing;
positioning the container above the detection structure; and
allowing the sample volume to pass from the container through the detection structure.

3. The method of claim 2, wherein the identification particles are selectively attached to specific target molecules.

4. The method of claim 3, further comprising:
after allowing the sample volume to pass from the container through the detection structure and before passing the plurality of identification particles through the detection structure, connecting a wicking member to an outlet of the detection structure.

5. The method of claim 4, further comprising:
after determining that a flow of the plurality of identification particles into the detection structure is sufficient, replacing the wicking member with a cap member, and wherein imaging the area encompassing the plurality of channels includes placing the detection structure in an imaging enclosure, illuminating the detection structure, and imaging the area of the detection structure encompassing the plurality of channels.

6. The method of claim 3, further comprising: removing unbound identification particles from the detection structure.

7. The method of claim 1, wherein, in a plan view, at least most of the plurality of pillars have a parallelogram form.

8. The method of claim 1, wherein an inlet to the detection structure receives the sample volume from a stream of fluid.

9. The method of claim 8, wherein the stream of fluid is provided via a pump.

10. The method of claim 1, wherein the target molecules comprise nucleic acid molecules, further comprising:
directing the target nucleic acid molecule to a nucleic acid analysis methodology that detects or identifies or quantifies the target nucleic acid molecule.

11. The method of claim 10, wherein the directing step comprises:
contacting the target nucleic acid molecules attached to the surfaces of the channels with a primer nucleic acid molecule and a polymerase enzyme to produce a target nucleic acid molecule copy; and
directing the target nucleic acid molecule copy to a nucleic acid analysis methodology that detects or identifies or quantifies the target nucleic acid molecule copy.

* * * * *

UNITED STATES PATENT AND TRADEMARK OFFICE
CERTIFICATE OF CORRECTION

PATENT NO. : 10,850,276 B2
APPLICATION NO. : 15/905290
DATED : December 1, 2020
INVENTOR(S) : John Gerdes, Kirsten Nelson and Kris Buchanan Page 1 of 1

It is certified that error appears in the above-identified patent and that said Letters Patent is hereby corrected as shown below:

In the Claims

In Claim 1, Column 15, Line 45, delete "dim" and insert --pillars-- therefore.

Signed and Sealed this
Twelfth Day of January, 2021

Andrei Iancu
*Director of the United States Patent and Trademark Office*